(12) United States Patent
Burbank et al.

(10) Patent No.: US 8,447,386 B2
(45) Date of Patent: *May 21, 2013

(54) MARKER OR FILLER FORMING FLUID

(75) Inventors: Fred H. Burbank, Laguna Niguel, CA (US); Michael L. Jones, San Clemente, CA (US); Frank Louw, Carlsbad, CA (US); Paul Lubock, Laguna Niguel, CA (US)

(73) Assignee: Senorx, Inc., Tempe, AZ (US)

( * ) Notice: Subject to any disclaimer, the term of this patent is extended or adjusted under 35 U.S.C. 154(b) by 223 days.

This patent is subject to a terminal disclaimer.

(21) Appl. No.: 12/967,639

(22) Filed: Dec. 14, 2010

(65) Prior Publication Data

US 2011/0092815 A1 Apr. 21, 2011

Related U.S. Application Data

(63) Continuation of application No. 10/444,428, filed on May 23, 2003, now Pat. No. 7,877,133.

(51) Int. Cl.
*A61B 6/00* (2006.01)
*A61B 10/00* (2006.01)

(52) U.S. Cl.
USPC .............................. 600/431; 600/432; 600/562

(58) Field of Classification Search
USPC ................. 600/431, 562; 604/11, 15
See application file for complete search history.

(56) References Cited

U.S. PATENT DOCUMENTS

| | | |
|---|---|---|
| 2,192,270 A | 3/1940 | McGowan |
| 2,481,408 A | 9/1949 | Fuller et al. |
| 2,832,888 A | 4/1958 | Houston |
| 2,899,362 A | 8/1959 | Sieger, Jr. et al. |
| 2,907,327 A | 10/1959 | White |
| 3,341,417 A | 9/1967 | Sinaiko |
| 3,402,712 A | 9/1968 | Eisenhand |
| 3,516,412 A | 6/1970 | Ackerman |

(Continued)

FOREIGN PATENT DOCUMENTS

| | | |
|---|---|---|
| DE | 1029528 B | 5/1958 |
| EP | 0146699 A1 | 7/1985 |

(Continued)

OTHER PUBLICATIONS

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

(Continued)

*Primary Examiner* — Rene Towa
*Assistant Examiner* — Adam Eiseman

(57) ABSTRACT

A system for at least partially filling and marking a cavity at a site within a patient's body includes a marker delivery device having a chamber configured to contain a marking substance and having a mechanism configured to expel the marking substance. A quantity of the marking substance is contained within the chamber of the marker delivery device. The marking substance is configured to at least partially fill the cavity and form therein a porous bioabsorbable body. A delivery tube is coupled in fluid communication with the chamber of the marker delivery device. The delivery tube has a distal end with a discharge port through which the marking substance is expelled. A releasable remotely detectable distal tip is coupled to the distal end of the delivery tube and is configured to be released to remain within the porous bioabsorbable body within the cavity upon the formation thereof.

20 Claims, 3 Drawing Sheets

U.S. PATENT DOCUMENTS

| | | |
|---|---|---|
| 3,593,343 A | 7/1971 | Viggers |
| 3,757,781 A | 9/1973 | Smart |
| 3,818,894 A | 6/1974 | Wichterle et al. |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,358,514 A | 10/1994 | Schulman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,842,477 A | 12/1998 | Naughton et al. |

| | | | | | | |
|---|---|---|---|---|---|---|
| 5,842,999 | A | 12/1998 | Pruitt et al. | 6,340,367 B1 | 1/2002 | Stinson et al. |
| 5,845,646 | A | 12/1998 | Lemelson | 6,343,227 B1 | 1/2002 | Crowley |
| 5,846,220 | A | 12/1998 | Elsberry | 6,347,240 B1 | 2/2002 | Foley et al. |
| 5,851,508 | A | 12/1998 | Greff et al. | 6,347,241 B2 | 2/2002 | Burbank et al. |
| 5,853,366 | A | 12/1998 | Dowlatshahi | 6,350,244 B1 | 2/2002 | Fisher |
| 5,865,806 | A | 2/1999 | Howell | 6,350,274 B1 | 2/2002 | Li |
| 5,869,080 | A | 2/1999 | McGregor et al. | 6,354,989 B1 | 3/2002 | Nudeshima |
| 5,871,501 | A | 2/1999 | Leschinsky et al. | 6,356,112 B1 | 3/2002 | Tran et al. |
| 5,876,340 | A | 3/1999 | Tu et al. | 6,356,782 B1 | 3/2002 | Sirimanne et al. |
| 5,879,357 | A | 3/1999 | Heaton et al. | 6,358,217 B1 | 3/2002 | Bourassa |
| 5,891,558 | A | 4/1999 | Bell et al. | 6,363,940 B1 | 4/2002 | Krag |
| 5,897,507 | A | 4/1999 | Kortenbach et al. | 6,371,904 B1 | 4/2002 | Sirimanne et al. |
| 5,902,310 | A | 5/1999 | Foerster et al. | 6,394,965 B1 | 5/2002 | Klein |
| 5,911,705 | A | 6/1999 | Howell | 6,403,758 B1 | 6/2002 | Loomis |
| 5,916,164 | A | 6/1999 | Fitzpatrick et al. | 6,405,733 B1 | 6/2002 | Fogarty et al. |
| 5,921,933 | A | 7/1999 | Sarkis et al. | 6,409,742 B1 | 6/2002 | Fulton, III et al. |
| 5,922,024 | A | 7/1999 | Janzen et al. | 6,424,857 B1 | 7/2002 | Henrichs et al. |
| 5,928,626 | A | 7/1999 | Klaveness et al. | 6,425,903 B1 | 7/2002 | Voegele |
| 5,928,773 | A | 7/1999 | Andersen | 6,427,081 B1 | 7/2002 | Burbank et al. |
| 5,941,439 | A | 8/1999 | Kammerer et al. | 6,450,937 B1 | 9/2002 | Mercereau et al. |
| 5,941,890 | A | 8/1999 | Voegele et al. | 6,450,938 B1 | 9/2002 | Miller |
| 5,942,209 | A | 8/1999 | Leavitt et al. | 6,471,700 B1 | 10/2002 | Burbank et al. |
| 5,948,425 | A | 9/1999 | Janzen et al. | 6,478,790 B2 | 11/2002 | Bardani |
| 5,954,670 | A | 9/1999 | Baker | 6,506,156 B1 | 1/2003 | Jones et al. |
| 5,972,817 | A | 10/1999 | Haines et al. | 6,511,468 B1 | 1/2003 | Cragg et al. |
| 5,989,265 | A | 11/1999 | Bouquet De La Joliniere et al. | 6,537,193 B1 | 3/2003 | Lennox |
| 6,015,541 | A | 1/2000 | Greff et al. | 6,540,981 B2 | 4/2003 | Klaveness et al. |
| 6,030,333 | A | 2/2000 | Sioshansi et al. | 6,544,185 B2 | 4/2003 | Montegrande |
| 6,053,925 | A | 4/2000 | Barnhart | 6,551,253 B2 | 4/2003 | Worm et al. |
| 6,056,700 | A | 5/2000 | Burney et al. | 6,554,760 B2 | 4/2003 | Lamoureux et al. |
| 6,066,122 | A | 5/2000 | Fisher | 6,562,317 B2 | 5/2003 | Greff et al. |
| 6,066,325 | A | 5/2000 | Wallace et al. | 6,564,806 B1 | 5/2003 | Fogarty et al. |
| 6,071,301 | A | 6/2000 | Cragg et al. | 6,565,551 B1 | 5/2003 | Jones et al. |
| 6,071,310 | A | 6/2000 | Picha et al. | 6,567,689 B2 | 5/2003 | Burbank et al. |
| 6,071,496 | A | 6/2000 | Stein et al. | 6,575,888 B2 | 6/2003 | Zamora et al. |
| 6,096,065 | A | 8/2000 | Crowley | 6,575,991 B1 | 6/2003 | Chesbrough et al. |
| 6,096,070 | A | 8/2000 | Ragheb et al. | 6,605,047 B2 | 8/2003 | Zarins et al. |
| 6,106,473 | A | 8/2000 | Violante et al. | 6,610,026 B2 | 8/2003 | Cragg et al. |
| 6,117,108 | A | 9/2000 | Woehr et al. | 6,613,002 B1 | 9/2003 | Clark et al. |
| 6,120,536 | A | 9/2000 | Ding et al. | 6,616,630 B1 | 9/2003 | Woehr et al. |
| 6,142,955 | A | 11/2000 | Farascioni et al. | 6,626,850 B1 | 9/2003 | Chau et al. |
| 6,159,445 | A | 12/2000 | Klaveness et al. | 6,628,982 B1 | 9/2003 | Thomas et al. |
| 6,161,034 | A | 12/2000 | Burbank et al. | 6,636,758 B2 | 10/2003 | Sanchez et al. |
| 6,162,192 | A | 12/2000 | Cragg et al. | 6,638,234 B2 | 10/2003 | Burbank et al. |
| 6,173,715 | B1 | 1/2001 | Sinanan et al. | 6,638,308 B2 | 10/2003 | Corbitt, Jr. et al. |
| 6,174,330 | B1 | 1/2001 | Stinson | 6,652,442 B2 | 11/2003 | Gatto |
| 6,177,062 | B1 | 1/2001 | Stein et al. | 6,656,192 B2 | 12/2003 | Espositio et al. |
| 6,181,960 | B1 | 1/2001 | Jensen et al. | 6,662,041 B2 | 12/2003 | Burbank et al. |
| 6,183,497 | B1 | 2/2001 | Sing et al. | 6,699,205 B2 | 3/2004 | Fulton, III et al. |
| 6,190,350 | B1 | 2/2001 | Davis et al. | 6,712,774 B2 | 3/2004 | Voegele et al. |
| 6,190,353 | B1 | 2/2001 | Makower et al. | 6,712,836 B1 | 3/2004 | Berg et al. |
| 6,200,258 | B1 | 3/2001 | Slater et al. | 6,716,444 B1 | 4/2004 | Castro et al. |
| 6,203,524 | B1 | 3/2001 | Burney et al. | 6,725,083 B1 | 4/2004 | Burbank et al. |
| 6,203,568 | B1 | 3/2001 | Lombardi et al. | 6,730,042 B2 | 5/2004 | Fulton et al. |
| 6,213,957 | B1 | 4/2001 | Milliman et al. | 6,730,044 B2 | 5/2004 | Stephens et al. |
| 6,214,045 | B1 | 4/2001 | Corbitt, Jr. et al. | 6,746,661 B2 | 6/2004 | Kaplan |
| 6,214,315 | B1 | 4/2001 | Greff et al. | 6,746,773 B2 | 6/2004 | Llanos et al. |
| 6,220,248 | B1 | 4/2001 | Voegele et al. | 6,752,154 B2 | 6/2004 | Fogarty et al. |
| 6,224,630 | B1 | 5/2001 | Bao et al. | 6,766,186 B1 | 7/2004 | Hoyns et al. |
| 6,228,049 | B1 | 5/2001 | Schroeder et al. | 6,774,278 B1 | 8/2004 | Ragheb et al. |
| 6,228,055 | B1 | 5/2001 | Foerster et al. | 6,780,179 B2 | 8/2004 | Lee et al. |
| 6,231,615 | B1 | 5/2001 | Preissman | 6,824,507 B2 | 11/2004 | Miller |
| 6,234,177 | B1 | 5/2001 | Barsch | 6,824,527 B2 | 11/2004 | Gollobin |
| 6,241,687 | B1 | 6/2001 | Voegele et al. | 6,846,320 B2 | 1/2005 | Ashby et al. |
| 6,241,734 | B1 | 6/2001 | Scribner et al. | 6,862,470 B2 | 3/2005 | Burbank et al. |
| 6,251,418 | B1 | 6/2001 | Ahern et al. | 6,863,685 B2 | 3/2005 | Davila et al. |
| 6,261,243 | B1 | 7/2001 | Burney et al. | 6,899,731 B2 | 5/2005 | Li et al. |
| 6,261,302 | B1 | 7/2001 | Voegele et al. | 6,918,927 B2 | 7/2005 | Bates et al. |
| 6,264,917 | B1 | 7/2001 | Klaveness et al. | 6,936,014 B2 | 8/2005 | Vetter et al. |
| 6,270,464 | B1 | 8/2001 | Fulton, III et al. | 6,939,318 B2 | 9/2005 | Stenzel |
| 6,270,472 | B1 | 8/2001 | Antaki et al. | 6,945,973 B2 | 9/2005 | Bray |
| 6,287,278 | B1 | 9/2001 | Woehr et al. | 6,951,564 B2 | 10/2005 | Espositio et al. |
| 6,287,332 | B1 | 9/2001 | Bolz et al. | 6,992,233 B2 | 1/2006 | Drake et al. |
| 6,289,229 | B1 | 9/2001 | Crowley | 6,994,712 B1 | 2/2006 | Fisher et al. |
| 6,306,154 | B1 | 10/2001 | Hudson et al. | 7,001,341 B2 | 2/2006 | Gellman et al. |
| 6,312,429 | B1 | 11/2001 | Burbank et al. | 7,008,382 B2 | 3/2006 | Adams et al. |
| 6,316,522 | B1 | 11/2001 | Loomis et al. | 7,014,610 B2 | 3/2006 | Koulik |
| 6,335,029 | B1 | 1/2002 | Kamath et al. | 7,025,765 B2 | 4/2006 | Balbierz et al. |
| 6,336,904 | B1 | 1/2002 | Nikolchev | 7,044,957 B2 | 5/2006 | Foerster et al. |

| | | |
|---|---|---|
| 7,083,576 B2 | 8/2006 | Zarins et al. |
| 7,125,397 B2 | 10/2006 | Woehr et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,637,948 B2 | 12/2009 | Corbitt, Jr. |
| 7,819,820 B2 | 10/2010 | Field et al. |
| 2001/0003791 A1 | 6/2001 | Burbank et al. |
| 2001/0006616 A1 | 7/2001 | Leavitt et al. |
| 2001/0033867 A1 | 10/2001 | Ahern et al. |
| 2001/0049481 A1 | 12/2001 | Fulton, III et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0038087 A1 | 3/2002 | Burbank et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0188196 A1 | 12/2002 | Burbank et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0162574 A1 | 8/2004 | Viola |
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0143656 A1 | 6/2005 | Burbank et al. |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0292690 A1 | 12/2006 | Liu et al. |
| 2007/0021642 A1 | 1/2007 | Lamoureux et al. |
| 2007/0057794 A1 | 3/2007 | Gisselberg et al. |
| 2007/0083132 A1 | 4/2007 | Sharrow |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0131825 A1 | 5/2009 | Burbank et al. |

FOREIGN PATENT DOCUMENTS

| | | |
|---|---|---|
| EP | 0255123 A2 | 2/1988 |
| EP | 0292936 A2 | 11/1988 |
| EP | 0386936 A1 | 9/1990 |
| EP | 0458745 A1 | 11/1991 |
| EP | 0481685 A1 | 4/1992 |
| EP | 0552924 A1 | 7/1993 |
| EP | 0475077 B1 | 6/1996 |
| EP | 0769281 A2 | 4/1997 |
| EP | 1281416 A2 | 6/2000 |
| EP | 1114618 A2 | 7/2001 |
| EP | 1163888 A1 | 12/2001 |
| EP | 1364628 A1 | 11/2003 |
| EP | 1493451 A1 | 1/2005 |
| EP | 1767167 A2 | 3/2007 |
| FR | 2646674 A3 | 11/1990 |

| | | |
|---|---|---|
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9608208 A1 | 3/1996 |
| WO | 9806346 A1 | 2/1998 |
| WO | 9908607 A1 | 2/1999 |
| WO | 9930764 A1 | 6/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0038579 A2 | 7/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Eiselt, P. et al, "Development of Technologies Aiding Large—Tissue Engineering", Biotechnol. Prog., vol. 14, No. 1, pp. 134-140, 1998.
Press release for Biopsys Ethicon Endo-Surgery (Europe) GmbH; The Mammotome Vacuum Biopsy System. From: http://www.medicine-news.com/articles/devices/mammotome.html. 3 pages.
Johnson & Johnson: Breast Biopsy (minimally invasive): Surgical Technique: Steps in the Mamotome Surgical Procedure. From http://www.jnjgateway.com. 3 pages.
Johnson & Johnson: New Minimally Invasive Breast Biopsy Device Receives Marketing Clearance in Canada; Aug. 6, 1999. From http://www.jnjgateway.com. 4 pages.
Johnson & Johnson: Mammotome Hand Held Receives FDA Marketing Clearance for Minimally Invasive Breast Biopises; Sep. 1, 1999. From From http://www.jnjgateway.com. 5 pages.
Johnson & Johnson: The Mammotome Breast Biopsy System. From: http://www.breastcareinfo.com/aboutm.htm. 6 pages.
Cook Incorporated: Emoblization and Occlusion. From: www.cookgroup.com 6 pages.
Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.
Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.
Fucci, V., et al., "Large Bowel Transit Times Using Radioopaque Markers in Normal Cats", J. of Am. Animal Hospital Assn., Nov.-Dec. 1995 31 (6) 473-477.
Schindlbeck, N. E., et al., "Measurement of Colon Transit Time", J. of Gastroenterology, No. 28, pp. 399-404, 1990.
Shiga, et al., Preparation of Poly(D, L-lactide) and Copoly(lactide-glycolide) Microspheres of Uniform Size, J. Pharm. Pharmacol. 1996 48:891-895.
Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206-No. 1.
H. J. Gent, M.D., et al., Stereotaxic Needle Localization and Cytological Diagnosis of Occult Breast Lesions, Annals of Surgery, Nov. 1986, pp. 580-584, vol. 204-No. 5.

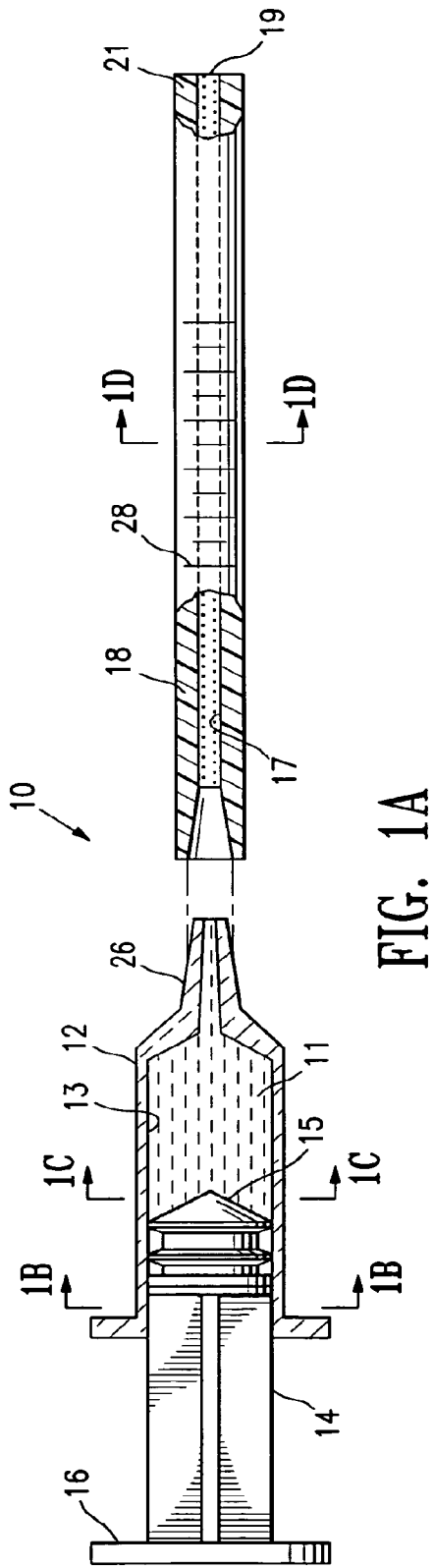
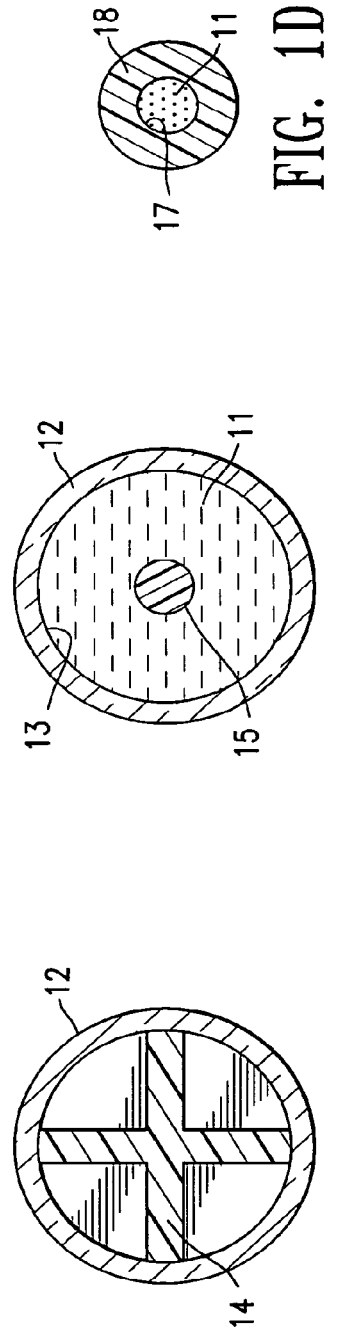
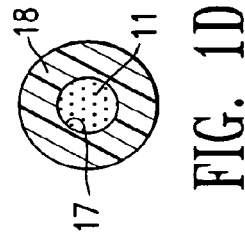
FIG. 1A
FIG. 1B
FIG. 1C
FIG. 1D

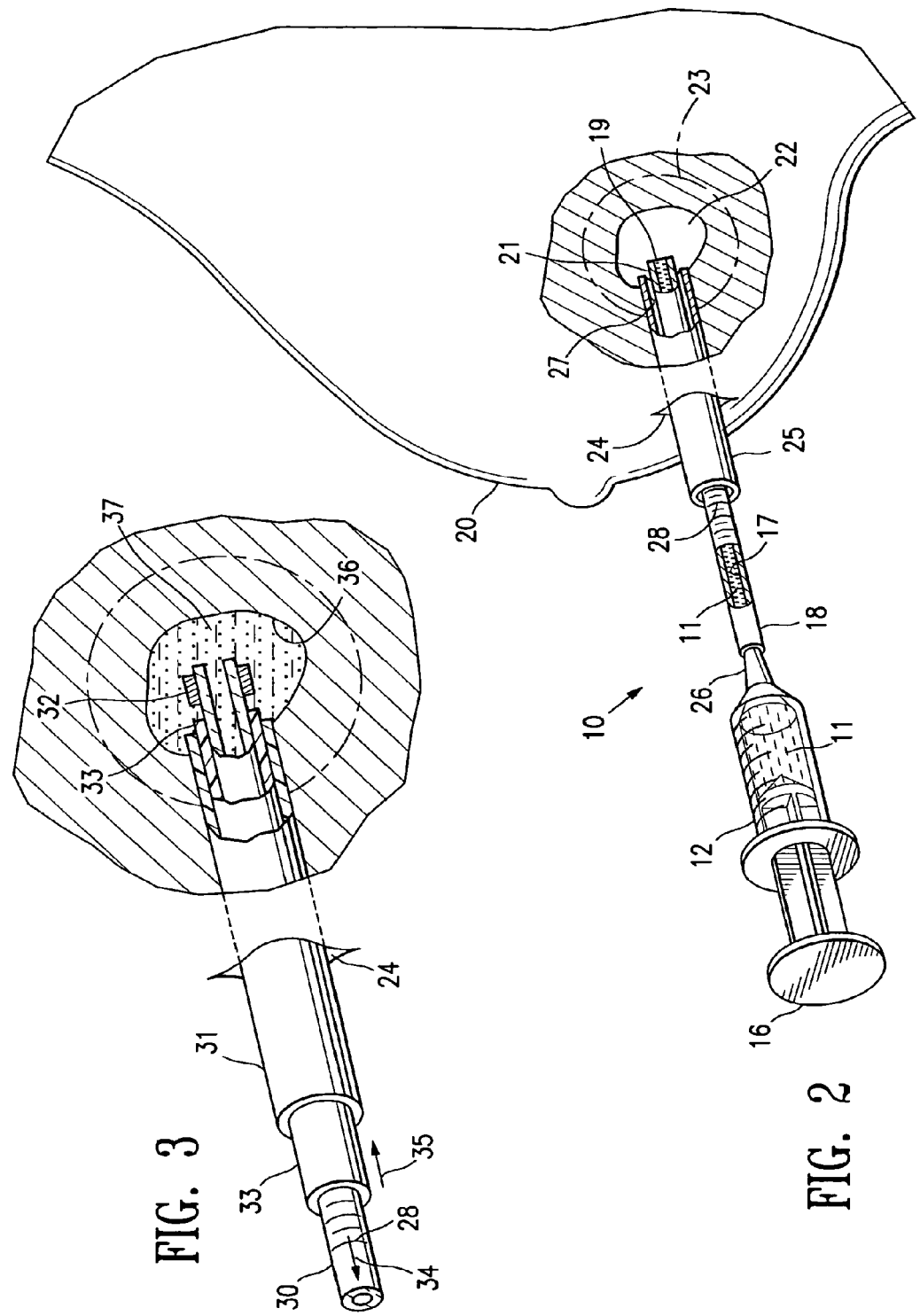

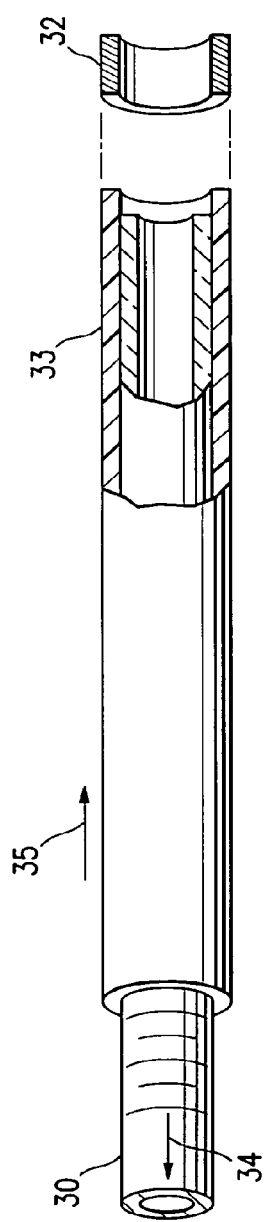
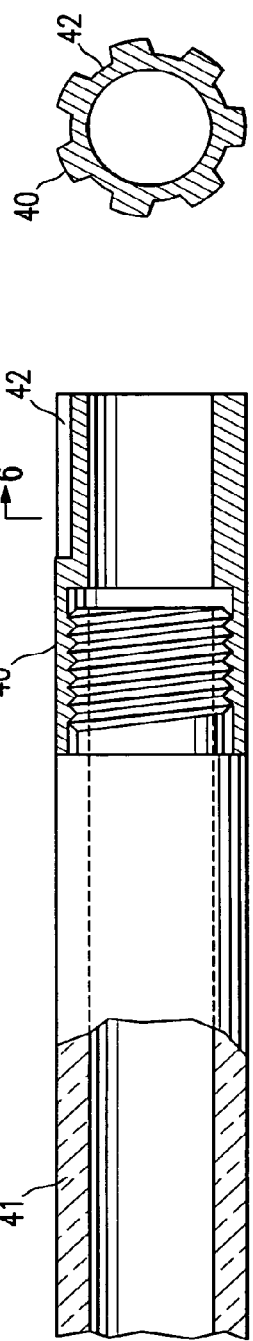
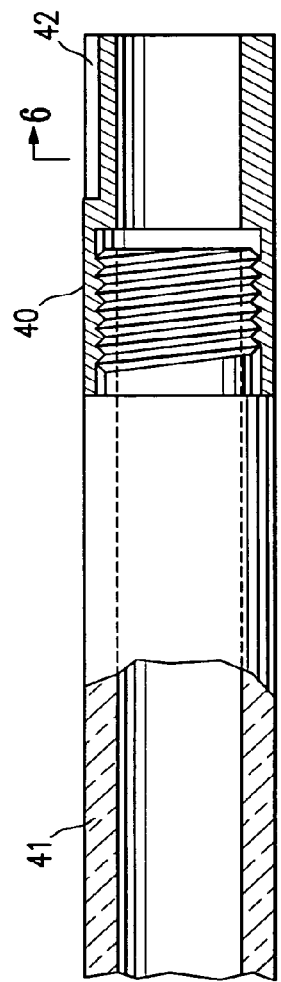
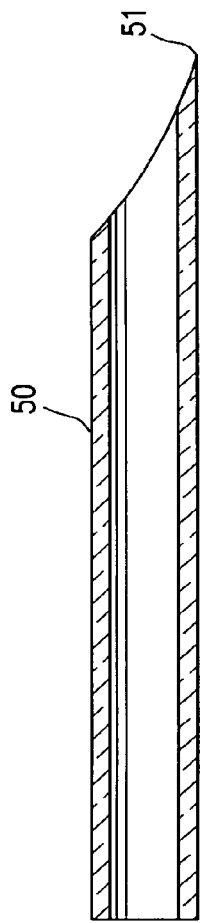
FIG. 4
FIG. 6
FIG. 5
FIG. 7

MARKER OR FILLER FORMING FLUID

CROSS REFERENCE TO RELATED APPLICATIONS

This is a continuation of U.S. patent application Ser. No. 10/444,428, entitled "MARKER OR FILLER FORMING FLUID", filed May 23, 2003 now U.S. Pat. No. 7,877,133, which is incorporated herein by reference.

FIELD OF INVENTION

This invention relates generally to the introduction of filler or marker material into a patient's body, and particularly to the filling a biopsy site within a patient's body from which a biopsy specimen has been taken with a mass of marker material.

BACKGROUND OF THE INVENTION

In diagnosing and treating certain medical conditions, it is often desirable to perform a biopsy, in which a specimen or sample of tissue is removed for pathological examination, tests and analysis. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a plan for the appropriate surgical procedure or other course of treatment. For example, breast biopsies may be taken where a suspicious lump or swelling is noticed in a breast. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

After the biopsy sample is taken, it may take several days or weeks before the results of the examination of the sample are obtained, and still longer before an appropriate treatment decision is reached. If the decision involves surgery it is clearly important for the surgeon to find the location in the breast from where the tumor tissue has been taken in the biopsy procedure, so that the entire tumor and possibly surrounding healthy tissue can be removed.

However, radiographically visible tissue features, originally observed in a mammogram, may be removed, altered or obscured by the biopsy procedure. In order for the surgeon or radiation oncologist to direct surgical or radiation treatment to the precise location of the breast lesion several days or weeks after the biopsy procedure was performed, it is desirable that a biopsy site marker be placed in or on the patient's body to serve as a landmark for subsequent location of the lesion.

Various types of biopsy site markers have been described, including visible markers applied externally to the patient's skin, radiographically (X-ray)-detectable tissue markers such as clips and staples, and ultrasound-detectable markers, have also been described. X-ray-detectable marker wires may be inserted through a biopsy needle, leading from the surface of the patient's body to the biopsy site. Some markers may be biodegradable.

However, due to the consistency of breast tissue and the fact that these biopsy site markers are typically introduced while the breast is still compressed between the mammography plates, prior art biopsy markers may not remain at the specific biopsy location after the breast has been decompressed and removed from the mammography apparatus, and may suffer from additional disadvantages as well. In order to locate an X-ray-detectable marker left at a biopsy site, an additional mammography is generally required at the time of follow up treatment or surgery. In addition, once it is located using mammography, the biopsy site must usually be marked again with a location wire that is visible by eye to provide guidance to the clinician performing the treatment or surgery. However, as the patient is removed from the mammography apparatus, or otherwise transported, the position of the location wire can change or shift before the treatment or surgery is performed, which may result in treatments being misdirected to undesired locations. Furthermore, at least some prior art biopsy site markers can remain present at the site of implantation for an indefinite period of time and, if not surgically removed, may obscure or otherwise interfere with any subsequent mammography or imaging studies.

However, due to the large amount of fibrous tissue normally present in a human breast, and due to the presence of ligaments running through the breast, a marker that simply has a bright signal alone will not provide a useful signal that is readily discernable from the many anatomic features normally present within a human breast. Such markers are typically small, being sized to fit within a syringe or other delivery tube, and so are often not readily distinguishable from natural features of the breast, which include occasional small ultrasound-bright spots.

As an alternative or adjunct to radiographic imaging, ultrasonic imaging and visualization techniques (abbreviated as "USI") can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. However, radiopaque markers may not be visible with USI. A marker visible with USI enables a follow-up procedure to be performed without the need for traditional radiographic mammography imaging which, as discussed above, can be subject to inaccuracies as a result of shifting of the location wire as well as being tedious and uncomfortable for the patient.

Thus, there is need in the art for biopsy site markers that are deliverable into the cavity created by removal of the biopsy specimen and not into tissue that is located outside of that biopsy cavity, and which will not migrate from the biopsy cavity even when the breast tissue is moved, manipulated or decompressed. Moreover, such desired markers should remain detectable at the biopsy site (i.e., within the biopsy cavity for a desired time period); should not interfere with imaging of the biopsy site and adjacent tissues at a later time; and should be readily distinguishable in the various imaging procedures from lines of calcifications which frequently are signs for a developing malignancy.

SUMMARY OF THE INVENTION

The invention is directed to the deployment of a marker or filler forming material at intracorporeal locations such as biopsy sites, sites for cosmetic treatments and other sites which may need additional bulk.

The invention, in one form thereof, is directed to a system for at least partially filling and marking a cavity at a site within a patient's breast from which tissue has been removed. The system includes a syringe having an elongated body, an inner bore, and a plunger slidably disposed within the inner bore. A delivery tube has a distal end with a discharge port and a delivery tube bore in fluid communication with the inner bore of the syringe and the discharge port. A quantity of marker forming fluid is within the inner bore of the syringe and is configured to at least partially fill the cavity at the biopsy site and form therein a porous bioabsorbable body. A releasable remotely detectable distal tip at the distal end of the delivery tube includes a radiopaque metal and is configured to remain within the porous bioabsorbable body within the cavity upon the formation thereof. The releasable remotely detectable radiopaque distal tip at the distal end of the delivery tube defines the discharge port.

The invention, in another form thereof, is directed to a system for at least partially filling and marking a cavity at a site within a patient's body from which tissue has been removed. The system includes a delivery device having a chamber configured to contain a marking substance. The marker delivery device has a mechanism configured to expel the marking substance. A quantity of the marking substance is contained within the chamber of the marker delivery device. The marking substance is configured to at least partially fill the cavity at the biopsy site and form therein a porous bioabsorbable body. A delivery tube is coupled in fluid communication with the chamber of the marker delivery device. The delivery tube has a distal end with a discharge port through which the marking substance is expelled. A releasable remotely detectable distal tip is coupled to the distal end of the delivery tube and is configured to be released to remain within the porous bioabsorbable body within the cavity upon the formation thereof.

The marker or filler material is formed intracorporeally from a biocompatible solution having as a solute bioabsorbable polymeric material which is relatively insoluble in body fluid or other water based fluids and a water soluble, non-aqueous polar solvent such as dimethyl sulfoxide (DMSO). Suitable bioaborbable polymers include polylactic acid, polyglycolic acid, polycaprolactones and copolymers and blends thereof. When the marker or filler forming fluid contacts body fluid or other water based fluids present at intracorporeal locations, the non-aqueous solvent is quickly absorbed by the body fluid or water based fluid present at the site, precipitating a mass of the water insoluble bioabsorbable polymeric material at the site. The polymeric material forming the marker or filler mass is preferably inherently ultrasonically detectable or the marker fluid may be treated to have a plurality of gas bubbles or otherwise aerated, so that upon formation of the polymeric mass at the site, gas is incorporated in the solid mass forming to provide ultrasonically detectable porosity.

The following description of embodiments of the invention is primarily directed to deployment of mass at a biopsy site for purposes of remote detection of the biopsy site. However, it should be recognized that the invention may be employed to form filling or bulking masses at an intracorporeal locations for cosmetic and other uses, as previously alluded to.

After a biopsy specimen is removed from the patient, a guiding member such as a cannula or other tubular member is preferably left within the patient with the distal end thereof within or close to the biopsy site in order to provide subsequent access to the biopsy site. The tubular guiding member may be part of the biopsy system such as a SenoCor 360™ or a Mammotome® system which was used to separate the tissue specimen and remove it from the site but which remains in place after the specimen has been removed. The marker forming fluid embodying features of the invention, may be suitably delivered by a syringe with an elongated delivery tube which at least in part fits within a tubular guiding member leading to the biopsy site.

Generally, the amount of polymeric solute ranges from about 1 to about 50%, preferably about 10 to about 35% by weight of the marker or filler forming fluid. The ratio of the polymer solute to the solvent can be varied to adjust the delivery characteristics and the in-vivo lifetime (i.e. the time period in which the polymeric mass is at the biopsy site). For example a lower percentage of polymeric material in the mix will provide a softer or more friable marker mass within the cavity, whereas a higher percentage will provide a firmer marker mass. Lower percentages of solvent will provide thicker marker fluids which will not be readily displaced from the biopsy site, whereas higher percentages will provide a less viscous solution which is easier to deliver. High molecular weight polylactic acid provides a longer in-vivo life time, e.g. up to a year or more. A lower molecular weight polymeric material such as a copolymer of lactic acid (90%) and glycolic acid (10%) provides an in-vivo life time of about two to three weeks. A copolymer of lactic acid (65%) and glycolic acid (35%) with a molecular weight of about 60 kD has an in-vivo lifetime of about 12 to 14 weeks.

An ultrasound-detectable marker typically must remain in place and be remotely detectable within a patient for at least 2 weeks to have any practical clinical value. Thus, an ultrasound-detectable marker material embodying features of the invention is detectable at a biopsy site within a patient for a time period of at least 2 weeks, preferably at least about 6 weeks, and may remain detectable for a time period of up to about 20 weeks or more. An ultrasound-detectable marker mass embodying features of the invention is preferably not detectable after about one year, and usually not more than about 6 months after placement at a biopsy site. More preferably, the ultrasound-detectable marker mass should not be detectable with ultrasound after about 12 weeks from placement at a biopsy site. A preferable in-vivo lifetime for an ultrasound-detectable biopsy marker mass having features of the invention is about 6 weeks to about 12 weeks.

The detectable marker mass which forms in the biopsy cavity should be large enough to fill a substantial portion, preferably all of the cavity. This allows the detection and definition of the boundaries of the biopsy cavity. The accessing passageway leading to the biopsy cavity may also at least in part be filled with the marker fluid as well if desired, which allows the physician to follow to locate the marker mass. The marker mass which forms in the cavity is ultrasonically detectable, but the marker fluid may also include ultrasonically or radiographically detectable powders or other particulate to augment the detection of the polymeric mass or the biopsy cavity. Other therapeutic and diagnostic agents may be incorporated into the marker fluid such as pharmaceutical agents, chemotherapeutic agents, anesthetic agents, hemostatic agents, pigments, dyes, radiopaque agents, materials detectable by magnetic resonance imaging (MRI), inert materials, and other compounds.

In one embodiment of the invention, the delivery system is employed to incorporate a radiopaque or other type of long term or permanent marker element within the polymeric mass which forms in the biopsy cavity. For example, the distal end of the syringe assembly or the tubular guide member leading to the biopsy site may be provided with a distal tip which is formed of radiopaque or other suitable material and which is releasably secured to the distal portion of the syringe or guide member so that upon formation of the marker mass from the marker fluid, the distal tip of the syringe or guide member can be released within the formed polymer marker mass and the syringe or guide member then removed from the mass.

The biopsy site markers formed by the present invention provide ultrasonically bright images which can be readily distinguished from the ultrasound signals arising naturally from within a breast or other tissue and which readily contrasts with the dark ultrasound shadow region immediately behind the bright ultrasound echo region. The strength of the reflected signal, and the contrast with the shadow region, make the marked site readily detectable even to relatively inexperienced surgeons. The in-vivo lifetime of the marker at the biopsy site can be preselected by adjusting the amount of polymeric material in the marker fluid and the molecular weight thereof. The employment of the filler forming functions of the solution may be advantageously utilized in cosmetic treatments similar to the uses of collagen, e.g. wrinkle removal or minimization, or in situations in which additional bulk is needed within a patient's body, e.g., treating for urinary incontinence.

These and other advantages will be evident from the following detailed description when taken in conjunction with the accompanying exemplary drawings.

BRIEF DESCRIPTION OF THE DRAWINGS

FIG. 1A is an elevational view, partially in section, of a marker fluid delivery system embodying features of the invention.

FIG. 1B is a transverse cross-sectional view taken along line 1B-1B shown in FIG. 1A.

FIG. 1C is a transverse cross-sectional view taken along line 1C-1C shown in FIG. 1A.

FIG. 1D is a transverse cross-sectional view taken along line 1D-1D shown in FIG. 1A.

FIG. 2 is a partially cut-away, perspective view of a system as illustrated in FIG. 1 shown depositing a marker fluid embodying features of the invention at a biopsy site within a breast of a female patient.

FIG. 3 is a perspective view, partially in section, of the distal portion of a delivery system having a releasable marker element on the distal tip of the delivery tube which acts as a long term or permanent marker.

FIG. 4 is a longitudinal, centerline cross-section of a delivery system having a releasable radiopaque distal tip.

FIG. 5 is a longitudinal, centerline cross-section of a delivery system having a releasable radiopaque distal tip which is threadably connected to the distal end of the delivery cannula and which has a grooved exterior to facilitate release of the distal tip.

FIG. 6 is a transverse cross-sectional view of the releasable distal tip shown in FIG. 5 taken along the lines 6-6.

FIG. 7 is an elevational view of a delivery cannula suitable for use to deliver the marker or filler forming fluid embodying features of the invention.

DETAILED DESCRIPTION OF THE INVENTION

FIGS. 1A-1D illustrate a system 10 for delivery of biopsy marker fluid 11 embodying features of the invention to a biopsy site within a patient's body. The system 10 includes a syringe 12 having a bore 13 containing a quantity of biopsy marker fluid 11. A plunger 14 with a sealable distal end 15 is slidably disposed within the bore 13 of syringe 12. Application of pressure to the head 16 of plunger 14 applies pressure to the fluid 11 and causes the discharge of fluid 11 from the bore 13 into the inner lumen 17 of delivery tube 18 secured to the discharge end of syringe 12. The marker fluid 11 passes through the inner lumen or bore 17 of the delivery tube 18 and out the discharge port 19 in the distal end of delivery tube 18.

As schematically illustrated in FIG. 1A, delivery tube 18 is secured to the syringe 12 by a friction fit. However, those skilled in the art will recognize that a variety of connections may be made between the syringe 12 and the delivery tube 18 such as a conventional luer-lock. The delivery tube 18 may have markings, such as lines or dots spaced at regular intervals along the length of the tube to indicate its position within the patient.

FIG. 2 illustrates the marker fluid delivery system 10 shown in FIGS. 1A-1D with the distal portion of the delivery tube 18 operatively disposed within a patient's breast 20 with the distal tip 21 of the delivery tube 18 disposed within biopsy cavity 22 at the biopsy site 23 ready to deliver marker fluid 11. An incision 24 in the breast 20 allows access to the cavity 22. Biopsy tubular guide member 25 extends through incision 24 in the patient's breast 20 into cavity 22 at biopsy site 23. The distal end 26 of syringe 12, containing marker fluid 11, is tightly engaged with delivery tube 18, which extends within guide member 25 so as to locate delivery tube outlet port 19 within biopsy cavity 22. The outer diameter of the delivery tube 18 is configured to allow the delivery tube to slidably fit inside the inner lumen 27 of biopsy guide member 25. Markings 28 spaced at regular intervals along the outer surface of delivery tube 18 indicate the depth of insertion of the tube within the guide member 25 and aid in the proper placement of discharge port 19 into position within cavity 22. Depression of plunger 14 of the syringe 12 forces marker fluid 11 out of syringe 12 through the inner lumen 17 of the delivery tube 18 and out port 19 into the cavity 22.

Fluid 11 mixes with body fluid or other water based fluid which may be present in the cavity 22. The solvent in fluid 11 is quickly dissolved in the body fluid or other water based fluid. The polymer solute which precipitates is relatively insoluble in the body fluid or other water based fluid which may be present in the cavity and forms a porous, ultrasonically detectable and bioabsorbable polymer mass 37 within the cavity 22. The mass 37 preferably essentially fills the biopsy cavity 22 so as to define the periphery of the biopsy cavity and to ensure that the mass remains within the biopsy cavity and will not migrate. The mass is subsequently absorbed by tissue and fluids near the biopsy site, so that at the end of the in-vivo life time of the bioabsorbable mass 37, the marker mass is no longer readily detectable at the site by ultrasonic means. Tissue ingrowth usually replaces the absorbed mass.

The preferred solvent for the fluid 11 is a pharmaceutical grade (USP) of DSMO. Other biocompatible water soluble, polar solvents are suitable. The preferred relatively water-insoluble bioabsorbable polymers are polylactic acid, poly glycolic acid, copolymers of lactic acid and glycolic acid, polycaprolactone. However, other suitable bioabsorbable, essentially water insoluble polymers include poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), poly(urethanes), poly(ester urethanes), polysaccharides, polylactic acid, polyglycolic acid, polycaproic acid, polybutyric acid, polyvaleric acid, and copolymers, polymer alloys, polymer mixtures, and combinations thereof.

The marker mass preferably essentially fills the biopsy cavity so as to define the periphery of the biopsy site cavity and to ensure that the marker mass remains within the biopsy cavity and will not migrate. The marker materials are resorbed by tissue and fluids near the biopsy site, so that, after their in-vivo life times, the marker materials are no longer USI-detectable at the biopsy site.

The marker fluid may also include radiopaque materials or radiopaque markers, so that the biopsy site may be detected both with ultrasound and with X-ray or other radiographic imaging techniques. Radiopaque materials and markers may include metal objects such as clips, bands, strips, coils, and other objects made from radiopaque metals and metal alloys, and may also include powders or particulate masses of radiopaque materials. Radiopaque markers may include liquid contrast agents such as Ethiodol or other non-water based contrast agents. Radiopaque markers may be of any suitable shape or size, and are typically formed in a recognizable shape not naturally found within a patient's body. Suitable radiopaque materials include stainless steel, platinum, gold, iridium, tantalum, tungsten, silver, rhodium, nickel, bismuth, other radiopaque metals, alloys and oxides of these metals, barium salts, iodine salts, iodinated materials, and combinations of these. The marker fluid may also include MRI-detectable materials or markers, so that the biopsy site may be detected with MRI techniques. MRI contrast agents such as gadolinium and gadolinium compounds, for example, are suitable for use with ultrasound-detectable biopsy marker materials embodying features of the invention. Colorants, such as dyes (e.g., methylene blue and carbon black) and pigments (e.g., barium sulfate), may also be included in the marker fluid of the invention. The colorant such as carbon black usually remains in the track or passageway leading to the marker or filler mass and this can be followed by the surgeon to the desired location.

Therapeutic agents to reduce bleeding, enhance clotting, to cause vasoconstriction, to prevent infections and other diseases, to reduce pain, chemotherapeutic agents to treat remnant cancer cells at the site may be incorporated into the marker fluid. Suitable therapeutic agents are provided in application Ser. No. 10/124,757, filed on Apr. 16, 2002, (now U.S. Pat. No. 6,862,470).

FIGS. 3 and 4 depict the distal portion of an alternative delivery tube 30 which is disposed within tubular guide 31 and which has a releasable radiopaque element 32 on the distal tip of the delivery tube. A cannula 33 is slidably disposed about the delivery tube 30. Relative longitudinal movement between the cannula 33 and delivery tube 30, as depicted by arrows 34 and 35, pushes the radiopaque element 32 off the end of the tube into the cavity 36 as shown in FIG. 4. When the marker fluid 37 containing a non-aqueous, water soluble solvent and a relatively water insoluble polymeric solute is injected into the biopsy cavity 36 and the polymer mass is formed, the radiopaque element 32 is released from the delivery tube 30 and left within the polymer mass. The radiopaque element 32 is released within the polymer mass at a point in the formation of the mass which ensures that the position of the radiopaque element 32 is maintained after the distal end of the delivery tube 30 is removed from the cavity 36. Preferably, the radiopaque element 32 is centrally located within the biopsy cavity 36.

FIGS. 5 and 6 illustrate an alternative embodiment in which a releasable radiopaque element 40 is the distal tip of delivery tube 41. As shown, the element 40 is threadably connected to the distal portion of the delivery tube 41 and has a grooved exterior 42 which helps to fix the tip in the polymeric mass. This allows the delivery tube 41 to be unscrewed from the tip element 40 and to be withdrawn from the patient, leaving the radiopaque tip 40 within the polymeric mass.

The releasable radiopaque element may have a variety of other shapes which are recognizable as not being naturally found within a patient's body to facilitate remote detection radiographically or ultrasonically. For example, the radiopaque may have an exterior transverse shape such as a star or a square. The radiographically detectable distal tip may be formed of a suitable radiopaque material such as stainless steel, platinum, gold, iridium, tantalum, tungsten, silver, rhodium, nickel, bismuth, other radiopaque metals, alloys and oxides of these metals. Radiopaque salts such as barium salts, iodine salts, iodinated materials, and combinations of these may be incorporated into polymeric or ceramic materials which form the releasable tip.

As shown in FIG. 7, the deployment system may have a delivery tube 50 with a needle-like distal tip 51 to facilitate advancement of the delivery tube through tissue to the target site. This embodiment is particularly suitable in those situations in which there is no guide tube or other cannula in place to provide access to the target site.

Markers embodying features of the present invention remain detectable at an intracorporeal site for a desired time period, and degrade or dissolve so as to not interfere with imaging of the biopsy site and adjacent tissues at a later time. Suitable marker materials typically do not migrate from the biopsy site before being dissolved or otherwise absorbed, and so provide reliable temporary marking of the location of a biopsy site and the margins thereof. The marker materials having features of the invention are readily distinguishable from natural body features including signs of a developing or an actual malignancy. The present invention also includes apparatus and method for delivering markers to a biopsy site.

The purpose of markers embodying features of the invention is to facilitate the location and performance of a surgical procedure that is performed while the marker is still detectable. The in-vivo lifetime of the marker mass remaining in the biopsy cavity is relatively short, e.g. less than one year, preferably less than about six months. Typically, the marker mass should have an in-vivo life time of about 6 to about 20 weeks, preferably 6 to 12 weeks. The disappearance of a marker after a longer period of time is required to avoid obscuring or interfering with follow-up imaging or further mammography.

Typically, the marker fluid embodying features of the present invention containing ultrasound-detectable solute of bioabsorbable polymeric material of the present invention is deposited at a biopsy site within a patient's body to form a biopsy marker mass at the site to allow for the subsequent location of the site by medical personnel. Thus, for example, a quantity of fluid formed of a non-aqueous water soluble solvent such as DSMO with a bioabsorbable polymeric material which is essentially insoluble in body fluids or other water based fluids is delivered into a cavity at a biopsy site. When the solution comes into contact with body fluid or other water based fluid at the biopsy site, the solvent is quickly dissolved in the body fluid and the relatively water insoluble polymeric solute forms a marker mass within the biopsy cavity.

The in-vivo lifetime of the polymeric material, i.e. the time period in which the polymeric mass is ultrasonically detectable, is related to the molecular weight of the polymer. For example, copolymers of lactic and glycolic acids having an initial molecular weight of about 45,000 Daltons (45 kD) before processing, are suitable for use in making an ultrasound-detectable marker material having an in-vivo lifetime of about 12 weeks. As is known to those of ordinary skill in the art, other materials, including other polymeric materials, may require a different starting molecular weight in order to obtain the same in-vivo lifetime. For example, polyglycolic acid typically degrades faster than other materials and as such requires a substantially higher initial molecular weight than polylactic acid or polycaprolactone to obtain a similar in-vivo lifetime.

Many properties of a material affects the intensity of its ultrasound reflection, including density, physical structure, molecular material, and shape. For example, sharp edges, or multiple reflecting surfaces on or within an object differing in density from its surroundings enhances its ability to be detected by ultrasound. Interfaces separating materials of different densities, such as between a solid and a gas, produce strong ultrasound signals.

The methods of the present invention provide materials having a porosity effective to produce strong ultrasound signals when located within the patient's biopsy cavity. The polymeric material may naturally form a porous mass or porosity can be formed by introducing a gas into the material during processing of a material, by release of gas from within the material, or by directing a gas into a material or by incorporating a blowing agent.

A typical human breast has a substantial number of features that are visualized with ultrasound. These features all have characteristic signals. Fibrous tissue or ligaments tend to show up as bright streaks, fat seems to appear as a dark gray area, the glandular tissue appears as a mottled medium gray mass. Cancerous lesions typically appear as a darker area with a rough outer edge which has reduced through transmission of the ultrasound energy. One advantage of the ultrasound-detectable biopsy marker materials of the present invention is that the materials provide an ultrasound signal which can be readily differentiated from anatomic structures within the breast, so that the identification and marking of a biopsy cavity does not require extensive training and experience.

The delivery syringe and the delivery tube attached to the syringe may be sized to accept any volume of marker or filler forming fluid desired to be injected into the desired intracorporeal site. The average Mammotome® biopsy removes about 0.5 to about 2, typically about 1 ml of tissue. The volume of marker fluid introduced into the biopsy cavity which remains after the removal of the tissue specimen is about the same as the tissue volume removed. Use of more marker fluid typically leads to some filling of the accessing passageway as well as of the cavity at the biopsy site. Smaller volumes of marker fluid may be used for smaller cavities at a biopsy site, such as are created with a single SenoCor 360™ biopsy or an automated Tru-Cut™ biopsy.

The solution embodying features of the invention may also be employed as a filler or bulking agent. For example, the filler forming fluid may be used in a manner similar to collagen for cosmetic purposes to minimize wrinkles, to fill pockmarks and other surface pits. The solution may also be used to bulk up an area of tissue for a variety of reasons. For example, if a radiation source for treating a tumor or a tumor site after removal of the tumor is located too close to the patient's skin, e.g. less than about 5 mm, the skin may be damaged or ultimately scarred by the irradiation. By deploying the filler forming fluid embodying features of the invention between the irradiation source and the skin, the damage or scarring to the skin can be reduced or eliminated. Depending upon the source of the radiation, either a single bolus or multiple bolus may be employed to bulk up the region and to displace the skin sufficiently to avoid damage.

The filler forming fluid embodying features of the invention may also be employed to provide a bulking mass about a urethra in the treatment of urinary incontinence, for a bulking mass about an anal sphincter for fecal incontinence and a bulking mass about an esophageal sphincter for gastroesophageal reflux disease. Other uses will become apparent to those skilled in the art.

While particular forms of the invention have been illustrated and described, it will be apparent that various modifications can be made without departing from the spirit and scope of the invention. Accordingly, it is not intended that the invention be limited to the specific embodiments illustrated and shall be defined by the scope of the appended claims as broadly as the prior art will permit. Moreover, those skilled in the art will recognize that features shown in one embodiment may be utilized in other embodiments. Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action.

What is claimed is:

1. A system for at least partially filling and marking a cavity at a site within a patient's breast from which tissue has been removed, comprising:
   a syringe having an elongated body, an inner bore, and a plunger slidably disposed within the inner bore;
   a delivery tube having a distal end with a discharge port and a delivery tube bore in fluid communication with the inner bore of the syringe and the discharge port;
   a quantity of marker forming fluid within the inner bore of the syringe configured to at least partially fill the cavity at the biopsy site and form therein a porous bioabsorbable body; and
   a releasable remotely detectable distal tip at the distal end of the delivery tube comprising radiopaque metal and configured to remain within the porous bioabsorbable body within the cavity upon the formation thereof,
   wherein the releasable remotely detectable radiopaque distal tip at the distal end of the delivery tube defines the discharge port.

2. The system of claim 1, wherein the releasable remotely detectable distal tip is threadably connected to the distal end of the delivery tube.

3. The system of claim 1, wherein the releasable remotely detectable distal tip is coupled to an external surface of the distal end of the delivery tube.

4. The system of claim 1, wherein the marker forming fluid comprises a non-aqueous solvent which is relatively soluble in a body fluid or other water based fluid, a bioabsorbable polymeric solute comprising a copolymer in the non-aqueous solvent which is relatively insoluble in body fluid or other water based fluid and which forms in the cavity the porous bioabsorbable body.

5. The system of claim 4, wherein the copolymer comprises about 65% (by wt.) polylactic acid and about 35% (by wt.) polyglycolic acid.

6. The system of claim 1, wherein the quantity of marker forming fluid in the inner bore of the syringe is about 0.2 ml to about 1.2 ml.

7. The system of claim 1, wherein a radiopaque part of the releasable remotely detectable radiopaque distal tip is formed of one or more materials selected from the group consisting of stainless steel, platinum, gold, iridium, tantalum, tungsten, silver, rhodium, nickel, bismuth, other radiopaque metals, alloys of radiopaque metals and mixtures of radiopaque metals, and combinations thereof.

8. The system of claim 1, wherein the marker forming fluid includes at least one agent selected from the group consisting of therapeutic or diagnostic agents.

9. The system of claim 8, wherein the agent is a hemostatic agent.

10. The system of claim 1, wherein the marker forming fluid includes a radioactive element.

11. The system of claim 10, wherein the radioactive element is a brachytherapy seed.

12. The system of claim 1, wherein the marker forming fluid contains about 1 to about 50% by weight water insoluble, bioabsorbable polymeric solute.

13. The system of claim 1, wherein the marker forming fluid contains about 10 to about 90% by weight water insoluble, bioabsorbable polymeric solute.

14. The system of claim 1, wherein the marker forming fluid is dimethyl sulfoxide.

15. A system for at least partially filling and marking a cavity at a site within a patient's body from which tissue has been removed, comprising:
- a marker delivery device having a chamber configured to contain a marking substance, the marker delivery device having a mechanism configured to expel the marking substance;
- a quantity of the marking substance contained within the chamber of the marker delivery device, the marking substance being configured to at least partially fill the cavity at the biopsy site and form therein a porous bioabsorbable body;
- a delivery tube coupled in fluid communication with the chamber of the marker delivery device, the delivery tube having a distal end with a discharge port through which the marking substance is expelled; and
- a releasable remotely detectable distal tip coupled to an external surface of the distal end of the delivery tube and configured to be released to remain within the porous bioabsorbable body within the cavity upon the formation thereof.

16. The system of claim 15, wherein the releasable remotely detectable distal tip at the distal end of the delivery tube comprises radiopaque metal.

17. The system of claim 15, wherein the marking substance in the chamber of the marker delivery device is a marker forming fluid.

18. The system of claim 17, wherein the marker forming fluid in the chamber of the marker delivery device comprises a non-aqueous solvent which is relatively soluble in a body fluid or other water based fluid, a bioabsorbable polymeric solute comprising a copolymer of polylactic acid and polyglycolic acid in a weight ratio of 90:10 to 60:40 in the non-aqueous solvent which is relatively insoluble in body fluid or other water based fluid and which forms in the cavity the porous bioabsorbable body.

19. The system of claim 17, wherein the marker forming fluid in the chamber of the marker delivery device is about 0.2 ml to about 1.2 ml.

20. A system for at least partially filling and marking a cavity at a site within a patient's body from which tissue has been removed, comprising:
- a marker delivery device having a chamber configured to contain a marking substance, the marker delivery device having a mechanism configured to expel the marking substance;
- a quantity of the marking substance contained within the chamber of the marker delivery device, the marking substance being configured to at least partially fill the cavity at the biopsy site and form therein a porous bioabsorbable body;
- a delivery tube coupled in fluid communication with the chamber of the marker delivery device, the delivery tube having a distal end with a discharge port through which the marking substance is expelled; and
- a releasable remotely detectable distal tip coupled to the distal end of the delivery tube and configured to be released to remain within the porous bioabsorbable body within the cavity upon the formation thereof, wherein the releasable remotely detectable distal tip forms an extension of the delivery tube to define the discharge port.

* * * * *